United States Patent [19]

Lüddecke et al.

[11] Patent Number: 5,895,659

[45] Date of Patent: Apr. 20, 1999

[54] FINELY DISPERSED CAROTENOID AND RETINOID SUSPENSION AND THEIR PREPARATION

[75] Inventors: Erik Lüddecke, Mutterstadt; Loni Schweikert, Altrip, both of Germany

[73] Assignee: BASF Akteingesellschaft, Ludwigshafen, Germany

[21] Appl. No.: 08/813,976

[22] Filed: Mar. 10, 1997

[30] Foreign Application Priority Data

Mar. 11, 1993 [DE] Germany ............... 196 09 538

[51] Int. Cl.⁶ .................. A23K 1/165; A23K 1/17
[52] U.S. Cl. .............. 424/442; 424/451; 424/461; 424/489
[58] Field of Search .................. 424/442, 450, 424/451, 489; 514/544

[56] References Cited

U.S. PATENT DOCUMENTS

| | | | |
|---|---|---|---|
| 3,998,753 | 12/1976 | Antoshkiw et al. | 242/312 |
| 4,435,427 | 3/1984 | Hoppe et al. | 424/356 |
| 4,522,743 | 6/1985 | Horn et al. | 252/311 |
| 4,726,955 | 2/1988 | Horn et al. | 426/73 |
| 5,091,187 | 2/1992 | Haynes | 424/450 |
| 5,091,188 | 2/1992 | Haynes | 424/450 |
| 5,453,447 | 9/1995 | End et al. | 514/763 |

*Primary Examiner*—Thurman K. Page
*Assistant Examiner*—William E. Benston, Jr.
*Attorney, Agent, or Firm*—Keil & Weinkauf

[57] ABSTRACT

Finely dispersed carotenoid or retinoid suspensions are prepared by dissolving the carotenoid or retinoid in a volatile, water-miscible organic solvent at 50° C.–250° C., where appropriate under elevated pressure, within less than 10 sec and immediately thereafter mixing the solution with an aqueous medium at from 0 to 90° C., wherein the mixing with the aqueous medium takes place in the absence of a protective colloid and in the presence of at least one physiologically tolerated emulsifier.

15 Claims, No Drawings

FINELY DISPERSED CAROTENOID AND RETINOID SUSPENSION AND THEIR PREPARATION

The invention relates to finely dispersed carotenoid and retinoid suspensions which can be used, for example, for coloring human and animal foods, and to a process for their preparation.

Carotenoids are pigments with a yellow to red color which are widespread in nature. They confer a characteristic coloring on many foodstuffs. Important representatives of the class of carotenoids are β-carotene, β-apo-8'-carotenal, canthaxanthin and citranaxanthin. These dyes can be prepared by synthesis and can be used as substitutes for synthetic dyes for coloring human and animal foods. They are additionally used in the pharmaceutical industry, for example because of their pro vitamin A activity.

In order to be employable as dyes in human and animal foods and in the pharmaceutical industry, the carotenoids and retinoids must be in a finely dispersed form because they are insoluble in water and have only low solubility in fats and oils. In addition, carotenoids and retinoids are very sensitive to oxidation.

Various processes for preparing finely dispersed carotenoids and retinoids are known.

In U.S. Pat. No. 5,091,188 and U.S. Pat. No. 5,091,187 phospholipid-coated microcrystals are described which are formulations of water insoluble pharmaceutical compounds which can be injected. A number of water insoluble pharmaceutical compounds, e.g. oxytetracycline (OTC), erythromycine, albendazol, nitroscanate or alphaxalone are formed in a dispersion of fine particles by using phospholipides like lecithin. Among the processes suggested for the preparation of the dispersions is the solvent dilution wherein solutions of the lipid and water-insoluble drug are prepared in an organic solvent like ethanol which is miscible with water. The solutions are expressed into an aqueous medium with high agitation, leaving behind the drug in microcrystaline form. The use of carotinoides or retinoides is not disclosed.

EP-B-0 065 193 describes a process for preparing finely dispersed carotenoid and retinoid products in powder form, wherein the carotenoid or retinoid is dissolved in a volatile, water-miscible, organic solvent at from 50° C. to 200° C., where appropriate under elevated pressure, within less than 10 sec, the carotenoid is immediately precipitated in the form of a colloidal dispersion from the resulting molecular solution by rapid mixing with an aqueous solution of a swellable colloid at from 0° C. to 50° C., and the solvent and the dispersing medium are removed from the resulting dispersion in a conventional way. Besides a swellable colloid, it is possible to employ a plasticizer and, where appropriate, stabilizers. Lecithin is mentioned as stabilizer which can be used. It is stated that the degree of fineness can be controlled by the choice of the stabilizers added to the carotenoid solution.

EP-A-0 479 066 discloses a process for the continuous preparation of β-carotene solubilizates by heating β-carotene together with an emulsifier until it dissolves, cooling the homogeneous solution to below 100° C. by adding water and subsequently adjusting the required final concentration.

Emulsifiers stated to be usable are ethoxylated triglycerides of fatty acids, ethoxylated sorbitan fatty acid esters and ethoxylated monohydroxy fatty acids. The β-carotene is heated together with the emulsifier for from 17 to 68 sec. The solubilizates contain no protective colloid.

EP-0 055 817 describes a process for preparing stable injectable β-carotene solubilizates. To do this, an emulsifier is heated to from 160 to 180° C., and β-carotene is introduced into the melt over about 5 minutes. After the β-carotene has dissolved, water is added to the solution, and it is cooled to from 60 to 80° C., resulting in the solubilizate. Emulsifiers stated to be usable are ethoxylated triglycerides of fatty acids, ethoxylated sorbitan fatty acid esters and ethoxylated monohydroxy fatty acids. The solubilizates contain no protective colloid.

It is an object of the present invention to provide finely dispersed carotenoid and retinoid suspensions in which it is possible to dispense with a protective colloid, and a process for their preparation.

It is another object of the present invention to provide a process for preparing finely dispersed carotenoid and retinoid suspensions, in which the carotenoids or retinoids are treated under mild conditions.

It is another object of the present invention to provide finely dispersed carotenoid and retinoid suspensions which are physiologically acceptable, and a process for their preparation.

It is another object of the present invention to provide finely dispersed carotenoid and retinoid suspensions and a process for their preparation, it being possible to vary the color of the resulting suspensions.

It is another object of the present invention to provide finely dispersed carotenoid and retinoid suspensions which have a high content of active ingredient and low viscosity, and a process for their preparation.

We have found that these objects are achieved according to the invention by suspensions and processes as described below.

Carotenoeds and Retinoids

The process according to the invention is preferably used to prepare finely dispersed carotenoid and retinoid suspensions.

Examples of carotenoids which can be used according to the invention are the known, available, natural or synthetic representatives of this class of compounds, for example carotene, lycopene, bixin, zeaxanthin, cryptoxanthin, citranaxanthin, lutein, canthaxanthin, astaxanthin, β-apo4'-carotenal, β-apo-8'-carotenal, β-apo-12'-carotenal, β-apo-8'-carotenoic acid and esters of hydroxyl- or carboxyl-containing compounds of this group, for example lower alkyl esters, preferably methyl and ethyl esters. These compounds can be used, for example, very satisfactorily as coloring agents. The industrially obtainable representatives such as β-carotene, canthaxanthin, β-apo-8'-carotenal and β-apo-8'-carotenoic esters are particularly preferred.

It is likewise possible to use retinoids, for example all-trans-retinoic acid, 13-cis-retinoic acid and the esters and amides of these acids. Compounds of this type which can be used are described by D. L. Newton, W. R. Henderson and M. B. Sporn in Cancer Research 40, (1980) 3413–3425.

SOLVENTS

A water-miscible organic solvent in which the carotenoids or retinoids employed are soluble at elevated temperature is used in the process according to the invention. Every suitable solvent can be used according to the invention, and preferably water-miscible, thermally stable, volatile solvents containing only carbon, hydrogen and oxygen are used. Examples of suitable solvents are alcohols, ethers, esters, ketones and acetals and mixtures thereof. Preferably used are ethanol, n-propanol, isopropanol, 1,2-butanediol 1-methyl ether, 1,2-propanediol 1-n-propyl ether or acetone, or a mixture of two or more thereof.

Solvents which are preferably used are those whose miscibility with water is at least 10% by volume, which have a boiling point below 200° C. and, where appropriate, have fewer than 10 carbon atoms in their structure.

The carotenoid or retinoid is, in one embodiment of the invention, employed in the dissolving in the form of a suspension in a volatile, water-miscible organic diluent or solvent, preferably in the solvent used in the dissolving, as described above.

EMULSIFIERS

Physiologically tolerated emulsifiers can be employed according to the invention for preparing the finely dispersed carotenoid and retinoid suspensions according to the invention.

The term "physiologically tolerated" means in this connection that the emulsifiers are physiologically acceptable on administration in the usual amounts to humans or animals and do not result in harm to the body.

This applies in particular to oral or intramuscular administration.

Emulsifiers which can be used according to the invention are listed hereinafter.

In a preferred embodiment of the invention, lecithin can be employed as emulsifier to prepare the finely dispersed carotenoid and retinoid suspensions according to the invention. Lecithins are also known under the name phosphatidylcholines and belong to the group of glycerophospholipids formed from fatty acids, glycerol, phosphoric acid and choline by esterification.

All suitable phosphatidylcholines can be used according to the invention, especially the naturally occurring phosphatidylcholines, which are is derivatives of 1,2-diacyl-sn-glycerol-3-phosphoric acids. It is possible to use phosphatidylcholines with identical or different fatty acid residues, and mixtures thereof.

A lecithin fraction from soybeans contains, for example, fatty acid residues from palmitic acid, stearic acid, palmitoleic acid, oleic acid, linoleic acid and linolenic acid.

It is possible to employ phosphatidylcholines with both unsaturated and saturated fatty acid residues.

In a particularly preferred embodiment of the invention, partially hydrolyzed lecithins are used to prepare the finely dispersed carotenoid and retinoid suspensions according to the invention, especially those which have a lysophospholipid content of 10–15% by weight. One example of a lecithin or lecithin mixture of this type is Emulfluid® E from Lucas Meyer GmbH.

In one embodiment of the invention, a mono-, di- or triglyceride of an aliphatic di- or polycarboxylic acid can be employed as emulsifier to prepare the finely dispersed carotenoid and retinoid suspensions according to the invention. The di- or polycarboxylic acid may have hydroxyl groups which are unsubstituted or substituted by acetyl radicals. Examples of acids which can be used are citric acid or tartaric acid. Examples of acid glycerides which can be used are citric esters of a mono- or diglyceride (for example Acidan N12® from Grinstedt), and diacetyltartaric esters of monoglycerides (DATEM, for example Panodan TR® from Grinstedt).

In one embodiment of the invention, a sugar fatty acid ester can be employed as emulsifier to prepare the finely dispersed carotenoid and retinoid suspensions according to the invention. It is possible in this case to use physiologically tolerated fatty acids such as lauric acid, palmitic acid, stearic acid or mono- or polyunsaturated fatty acids such as linoleic acid or linolenic acid. The sugar residue can be any suitable sugar residue, preferably an ascorbyl radical. One example of a sugar fatty acid ester which can be used is ascorbyl palmitate.

It is furthermore possible to use the emulsifiers as described, for example, in EP-A-0 479 066 or EP-A-0 055 817.

It is furthermore possible to use salts of physiologically tolerated fatty acids as described above, and mono- and diglycerides of these fatty acids. The mono- and diglycerides of these fatty acids may, where appropriate, be esterified with fruit acids.

In one embodiment of the invention, it is furthermore possible to use polyglycerol esters of these fatty acids.

Lecithin is preferably employed as emulsifier to prepare the finely dispersed carotenoid and retinoid suspensions according to the invention.

The emulsifiers which can be used according to the invention, especially lecithin, are physiologically acceptable and can thus be used in pharmaceutical compositions.

It has furthermore been found according to the invention that the emulsifiers which can be used according to the invention, especially the lecithin which is used in one embodiment, have a very fast emulsifying action, which makes it possible to use them in a high-speed process for preparing finely dispersed carotenoid and retinoid suspensions.

It has been found according to the invention that it is possible to dispense with the use of a protective colloid on use of the emulsifiers according to the invention, especially of lecithin, in the preparation of finely dispersed carotenoid and retinoid suspensions. The omission of a protective colloid leads to liquid carotenoid and retinoid suspensions with a lower viscosity and a higher content of active ingredient. In addition, especially for pharmaceutical applications, the number of ingredients in the suspensions is reduced, so that fewer interfering compounds which may have an effect on the activity of the carotenoids and/or retinoids are present.

The emulsifier used according to the invention, especially the lecithin, can in the process according to the invention be present in the aqueous medium and/or in the organic solvent. Thus, the emulsifier used according to the invention, especially the lecithin, can be present either in the suspension, prepared before the dissolving, of the carotenoid in the water-miscible organic solvent, or alternatively in the water-miscible organic solvent which is at elevated temperature. The emulsifier used according to the invention, especially the lecithin, is preferably added both to the organic carotenoid and retinoid suspension and to the aqueous medium.

The ratio of the amounts of emulsifier used according to the invention, especially lecithin, to carotenoid or retinoid can be chosen as desired, as long as finely dispersed carotenoid and retinoid suspensions which are stable are obtained.

The ratio of emulsifier used according to the invention, especially of lecithin, to carotenoid or retinoid in the suspension is preferably from 0.1 to 5 (ratio of the parts by weight). The ratio is particularly preferably 0.5 to 2, in particular 0.7 to 1.

It is furthermore possible to change the color of the resulting carotenoid and retinoid suspensions by changing the ratio of amounts of emulsifier used according to the invention, especially lecithin, to carotenoid or retinoid. With high proportions of emulsifier used according to the invention, especially lecithin, for example with a ratio of 2:1 by weight of emulsifier used according to the invention, especially lecithin, to carotene, the resulting products tend to be yellowish, and in the case of carotene and lecithin as emulsifier the latter is at least partially dissolved in the lecithin. With lower proportions of emulsifier used according to the invention, especially lecithin, relative to carotenoid, such as 0.75:1, for example β-carotene remains particulate. The color of the suspension is reddish brown in this case.

This variability of the color is advantageous for use of the carotenoid and retinoid suspensions of the present invention as food dye because it is simple to adapt the color depending on the specific use.

Furthermore, the omission of protective colloids in the carotenoid and retinoid suspensions makes it possible to prepare low-viscosity suspensions with high contents of active ingredient, for example of up to 10% by weight based on the finished suspension. This simplifies the use and the transport of the suspensions, because even with high contents of active ingredient they are still able to flow and be metered satisfactorily.

For example, this simplifies the use of β-carotene in the coloring of beverages because liquid metering devices can be used, which generally operate more precisely than solid metering devices in manufacturing plants.

Another advantage of the omission of protective colloids is that the suspensions can be used better in pharmaceutical applications. For example, the suspensions prepared according to the invention can be used as injection solutions, for example in veterinary medicine.

ANTIOXIDANTS

An antioxidant can be added in the process according to the invention to the water-miscible organic solvent or to the aqueous medium, to the finished suspension of the carotenoid or retinoid and to the carotenoids and retinoids. The antioxidant is used to increase the stability of the active ingredient to oxidative breakdown. The antioxidant if used is preferably dissolved together with the carotenoids or retinoids in the water-miscible organic solvent. Examples of antioxidants which can be used are α-tocopherol, t-butylhydroxytoluene, t-butylhydroxyanisole or ethoxyquin. Other suitable antioxidants can also be used.

PREPARATION PROCESS

The carotenoid and retinoid suspensions are prepared according to the invention by dissolving the carotenoid or retinoid in a volatile, water-miscible organic solvent at from 50° C. to 250° C., preferably 150 to 200° C., where appropriate under elevated pressure, within less than 10 sec, and immediately thereafter mixing the solution with an aqueous medium at from 0 to 90° C., preferably 2–50° C. A procedure of this type is described, for example, in EP-B1-0 065 193. The process described in this patent can be used according to the present invention.

The emulsifier used according to the invention can be present in the aqueous medium and/or in the organic diluent or solvent. The emulsifier, preferably lecithin, is preferably present in the aqueous medium and in the organic diluent or solvent.

In one embodiment of the invention, the emulsifier used according to the invention, preferably lecithin, is added to the water-miscible organic solvent used to prepare the initial suspension of the carotenoid or retinoid, as well as to the aqueous medium, preferably water.

If required, the emulsifier used according to the invention can also be present in the heated organic solvent.

Then, in one embodiment of the invention, a suspension of the carotenoid or retinoid in the water-miscible organic solvent is prepared. The water-miscible organic solvent used is preferably the same as is used as heated organic solvent in the subsequent step. In one embodiment of the invention, the concentration of the carotenoid or retinoid in this suspension is 2 to 40% by weight, based on the mixture. This suspension or the carotenoid or retinoid is then, in one embodiment of the invention, dissolved in heated water-miscible organic solvent within less than 10 sec, preferably less than 5 sec, particularly preferably less than 2 sec, in particular in fractions of a second. In this case, heated solvent is at from 50 to 200° C., preferably 100 to 180° C., particularly preferably 140 to 180° C. After the time for dissolving the carotenoid or retinoid in the heated water-miscible organic solvent, the solution is immediately thereafter mixed with an aqueous medium, at from 0 to 50° C. Water is preferably used as aqueous medium. Mixing the solution with the aqueous medium results in a fine dispersion of the carotenoid or retinoid.

The very short time needed to dissolve the carotenoid or retinoid means that the carotenoid or retinoid is exposed to an elevated temperature for only a very short time and is then immediately cooled again. This makes it possible for the carotenoids and/or retinoids to be treated under very mild conditions, and reduces the risk of oxidation or decomposition of the active ingredients. Compared with the process according to the invention, for example, when the active ingredient and solvent are heated together the carotenoid or retinoid is exposed to an elevated temperature for a considerably longer time until it dissolves, and this is associated with the risk of oxidation and/or thermal decomposition of the active ingredient.

In a preferred embodiment of the invention, the process is carried out continuously in two mixing chambers. This entails first a suspension of the active ingredient in the organic solvent being prepared and, for example by means of pumps, being fed into a first mixing chamber, into which the heated organic solvent is fed simultaneously, so that the active ingredient dissolves in the water-miscible organic solvent in the first mixing chamber at from 50 to 200° C. The active ingredient concentration in this first mixing chamber is preferably 0.5 to 10% by weight based on the solution. The volume of the mixing chamber is preferably such that the residence time of the active ingredient suspension and the solvent in the chamber is preferably less than 1 sec at the chosen delivery rate of the pumps.

The solvent is preferably brought to the required temperature by a heat exchanger before entering the mixing chamber, while the active ingredient suspension is kept at below 50° C. by being fed through a thermally insulated feed line. The mixing in the first mixing chamber is preferably turbulent. After a short residence time, preferably of less than 1 sec, the solution enters a second mixing chamber in which, for example by a pump, water or an aqueous medium is admixed, and the finely dispersed carotenoid and retinoid suspension is precipitated. The finely dispersed active ingredient suspension can then be discharged from the second mixing chamber through another line and fed, for example, into a reservoir. To maximize the active ingredient concentration, the suspension can be circulated back to the second mixing chamber.

The concentration of the carotenoid or retinoid in the suspension is in this case preferably 0.1 to 100 g/l.

If the pressure exceeds 1 bar, solvents can be used at temperatures above their boiling point (under atmospheric pressure).

In one embodiment of the invention, a product in powder form can be obtained from the resulting suspension, for example by the process described in DE-A 2 534 091 by spray-drying or spray-cooling or by enveloping the particles, removing and drying in a fluidized bed.

The spray-drying process is described, for example, also in EP-B1-0 065 193.

In one embodiment of the invention it is possible to remove, at least partially, the water-miscible organic solvent and/or the aqueous medium from the prepared carotenoid or retinoid suspension, in order to prepare a concentrated carotenoid or retinoid suspension. In this case, the concentration of the carotenoid or retinoid in the suspension can be 0.1 to 100 g/l.

It is possible by adjusting suitable quantity flows to obtain a carotenoid or retinoid suspension with a very small particle size of active ingredient. The particle size in the carotenoid or retinoid suspension is essentially <1 μm, preferably in the range from 0.01 to 0.4 μm, particularly preferably in the range from 0.03 to 0.2 μm.

It is possible, for example, to obtain a suspension with an average particle size of active ingredient of 0.03 μm at a carotene concentration of 0.1% by weight based on the finished suspension. In this case, the suspension has the appearance of a transparent carotene "solution". If the active ingredient content is higher, it is possible in one embodiment of the invention to increase the particle size. For example, it can average 0.06 μm in a 0.4% by weight solution. It is possible by concentrating the resulting suspension to achieve an active ingredient content of from 1 to 10% by weight based on the finished suspension. This can take place, for example, by evaporation under mild conditions or by membrane filtration. The resulting suspensions are stable on storage and have a virtually unchanged high specific color strength. The organic solvent employed can, where appropriate, be removed from the product, depending on the concentration step used. In a preferred embodiment, isopropanol or ethanol is used as solvent, and the carotenoid or retinoid is dissolved at about 180° C. in an excess of preheated alcohol so that a homogeneous solution is produced.

On mixing with water, which is the aqueous medium preferably used, the alcohol dissolves instantaneously in the water, resulting in an extremely finely dispersed suspension of the carotenoid or retinoid.

The invention is explained in detail hereinafter by means of an exemplary embodiment.

EXAMPLE 1

12.5 g of β-carotene are dissolved in 490 g of a solution of 9 g of lecithin (Emulfluid® E, Lucas Meyer GmbH, prepared by specific partial hydrolysis of natural lecithin, with a lysophospholipid content of 10–15% by weight, an HLB of 8–9) and 1.8 g of d,l-α-tocopherol in isopropanol (azeotrope) and mixed in a first mixing chamber with 775 g of isopropanol (azeotrope) which has been heated to 220° C. in a heat exchanger. At a metering rate of about 2 l/h for the suspension and 3 l/h for the heated solvent, the residence time in the mixing chamber is 0.35 sec. This results, at 190° C., in a molecular solution which is then fed into a second mixing chamber in which it is subjected to turbulent mixing with 7800 g of water (metering rate about 30 l/h). This results in formation of the finely dispersed carotene suspension, which is transferred into a collecting vessel. A clear orange suspension of carotene is obtained in the collecting vessel. The concentration of active ingredient in this case is 0.1% by weight based on the finished suspension, and the specific color strength (extinction at a path length of 1 cm at the maximum of the absorption band of a preparation diluted to an active ingredient content of 5 ppm with water) is 0.72. Particle size analysis by photon correlation spectroscopy reveals an average particle size of 70 nm.

EXAMPLE 2

120 g of β-carotene are dissolved in 540 g of a solution of 43 g of lecithin (Emulfluid® E, Lucas Meyer GmbH, see Example 1) and 17 g of d,l-α-tocopherol in isopropanol (azeotrope) and mixed in a first mixing chamber with 825 g of isopropanol (azeotrope) which has been heated to 220° C. in a heat exchanger. At a metering rate of about 2 l/h for the suspension and 3 l/h for the heated solvent, the residence time in the mixing chamber is 0.35 sec. This results, at 190° C., in a molecular is solution which is then fed into a second mixing chamber in which it is subjected to turbulent mixing with 8800 g of a solution of 43 g of lecithin in 10,400 g of water (metering rate about 30 l/h). This results in formation of the finely dispersed carotene suspension, which is transferred into a collecting vessel. An orange suspension of carotene is obtained in the collecting vessel. The concentration of active ingredient in this case is 1% by weight based on the finished suspension, and the specific color strength (extinction at a path length of 1 cm at the maximum of the absorption band of a preparation diluted to an active ingredient content of 5 ppm with water) is 0.67. Particle size analysis by photon correlation spectroscopy reveals an average particle size of 160 nm.

EXAMPLE 3

12.5 g of β-carotene are dissolved in 490 g of a solution of 1.8 g of citric ester of a mono/diglyceride (Acidan N12® from Grinstedt) and 1.8 g of d,l-α-tocopherol in isopropanol (azeotrope) and mixed in a first mixing chamber with 775 g of isopropanol (azeotrope) which has been heated to 220° C. in a heat exchanger. At a metering rate of about 2 l/h for the suspension and 3 l/h for the heated solvent, the residence time in the mixing chamber is 0.35 sec. This results, at 190° C., in a molecular solution which is then fed into a second mixing chamber in which it is subjected to turbulent mixing with 7800 g of water (metering rate about 30 l/h). This results in formation of the finely dispersed carotene suspension, which is transferred into a collecting vessel. A clear orange suspension of carotene is obtained in the collecting vessel. The concentration of active ingredient in this case is 0.1 % by weight based on the finished suspension, and the specific color strength (extinction at a path length of 1 cm at the maximum of the absorption band of a preparation diluted to an active ingredient content of 5 ppm with water) is 0.66. Particle size analysis by photon correlation spectroscopy reveals an average particle size of 80 nm.

EXAMPLE 4

25 g of β-carotene are dissolved in 950 g of a solution of 3.6 g of diacetyltartaric ester of monoglycerides (Panodan TR® from Grinstedt) and 3.6 g of d,l-α-tocopherol in isopropanol (azeotrope) and mixed in a first mixing chamber with 1300 g of isopropanol (azeotrope) which has been heated to 220° C. in a heat exchanger. At a metering rate of about 2 l/h for the suspension and 3 l/h for the heated solvent, the residence time in the mixing chamber is 0.35 sec. This results, at 190° C., in a molecular solution which is then fed into a second mixing chamber in which it is subjected to turbulent mixing with 15,400 g of water (metering rate about 30 l/h). This results in formation of the finely dispersed carotene suspension, which is transferred into a collecting vessel. A clear orange suspension of carotene is obtained in the collecting vessel. The concentration of active ingredient in this case is 0.14% by weight based on the finished suspension, and the specific color strength (extinction at the maximum of the absorption band of a preparation diluted to an active ingredient content of 5 ppm with water) is 0.72. Particle size analysis by photon correlation spectroscopy reveals an average particle size of 220 nm.

EXAMPLE 5

25 g of β-carotene are dissolved in 290 g of a solution of 3.6 g of ascorbyl palmitate and 3.6 g of d,l-α-tocopherol in isopropanol (azeotrope) and mixed in a first mixing chamber with 350 g of isopropanol (azeotrope) which has been heated to 220° C. in a heat exchanger. At a metering rate of about 2 l/h for the suspension and 3 l/h for the heated solvent, the residence time in the mixing chamber is 0.35 sec. This results, at 190° C., in a molecular solution which is then fed into a second mixing chamber in which it is subjected to turbulent mixing with 4150 g of water (metering rate about 30 l/h). This results in formation of the finely dispersed carotene suspension, which is transferred into a collecting vessel. A clear orange suspension of carotene is obtained in the collecting vessel. The concentration of active ingredient in this case is 0.5% by weight based on the finished suspension, and the specific color strength (extinction at the maximum of the absorption band of a preparation diluted to an active ingredient content of 5 ppm with water) is 0.69. Particle size analysis by photon correlation spectroscopy reveals an average particle size of 120 nm.

The prepared suspensions of β-carotene are physiologically acceptable and stable on storage for a long time. The β-carotene used in the preparation process is treated under very mild conditions because it is present in the heated solvent for only a very short time (0.35 seconds). The color of the finely dispersed carotenoid suspension varies because of the differences in particle size so that the color can be adjusted and varied depending on the way the process is carried out. The carotenoid suspensions have a high active ingredient content and low viscosity so that dividing into portions is simple, for example in the production of beverages.

We claim:

1. A process for preparing finely dispersed carotenoid or retinoid suspensions by dissolving the carotenoid or retinoid in a volatile, water-miscible organic solvent at 50° C.–250° C., where appropriate under elevated pressure, within less than 10 sec, and immediately thereafter mixing the solution with an aqueous medium at from 0 to 90° C., wherein the mixing with the aqueous medium takes place in the absence of a protective colloid and in the presence of at least one physiologically tolerated emulsifier.

2. A process as claimed in claim 1, wherein the particle size in the carotenoid or retinoid suspension is essentially less than 1 μm, preferably 0.01–0.4 μm, preferably 0.03–0.2 μm.

3. A process as claimed in claim 1, wherein the water-miscible volatile solvent is at least one alcohol, ketone, ester, acetal or ether or a mixture of one or more thereof, preferably acetone, 1,2-butanediol 1-methyl ether, 1,2-propanediol 1-n-propyl ether, ethanol, n-propanol, isopropanol or a mixture of two or more thereof.

4. A process as claimed in claim 1, wherein lecithin, a fatty acid salt, a mono-, di- or triglyceride of $C_{12}$–$C_{18}$-fatty acids or aliphatic, possibly acetylated, polycarboxylic acids, possibly esterified with fruit acids, a sugar fatty acid ester, or a polyglycerol ester of $C_{12}$–$C_{18}$-fatty acids is used as physiologically tolerated emulsifier.

5. A process as claimed in claim 1, wherein the carotenoid or retinoid is employed in the dissolving in the form of a suspension in a volatile, water-miscible organic diluent or solvent, preferably in the solvent used in the dissolving.

6. A process as claimed in claim 1, wherein the dissolving of the carotenoid or retinoid in the volatile, water-miscible organic solvent takes place in a mixing chamber, and the mixing of the solution with an aqueous medium takes place in a second mixing chamber which is connected in series with the first mixing chamber, and the process is chosen to be carried out continuously.

7. A process as claimed in claim 1, wherein the water-miscible organic solvent and/or the aqueous medium is at least partially removed from the carotenoid or retinoid suspension the carotenoid or retinoid suspension preferably being spray-dried to give a finely dispersed powder.

8. A process as claimed in claim 1, wherein the concentration of the carotenoid or retinoid in the suspension is from 0.1 to 100 g/l.

9. A process as claimed in claim 1, wherein the ratio of emulsifier to carotenoid or retinoid in the suspension is from 0.1 to 5, preferably 0.5 to 2, by weight.

10. A process as claimed in claim 1, wherein the water-miscible organic solvent or, where appropriate, the suspension of the carotenoid or retinoid contains an antioxidant, preferably tocopherol.

11. A carotenoid or retinoid suspension with a particle size of less than 1 μm in a water-containing medium, wherein the suspension contains no protective colloids and contains an emulsifier selected from lecithin, mono-, di- or triglycerides of aliphatic, possibly acetylated, polycarboxylic acids, preferably citric acid or tartaric acid, or ascorbyl palmitate.

12. A suspension as claimed in claim 11, characterized by one or more of the following features:

the particle size in the carotenoid or retinoid suspension is essentially less than 1 μm, preferably 0.01–0.4 μm, preferably 0.03–0.2 μm;

lecithin, a fatty acid salt, a mono-, di- or triglyceride of $C_{12}$–$C_{18}$-fatty acids or aliphatic, possibly acetylated, polycarboxylic acids, possibly esterified with fruit acids, a sugar fatty acid ester, or a polyglycerol ester of $C_{12}$–$C_{18}$-fatty acids is used as physiologically tolerated emulsifier;

the carotenoid or retinoid in the suspension is from 0.1 to 100 g/l;

the ratio of emulsifier to carotenoid or retinoid in the suspension is from 0.1 to 5, preferably 0.5 to 2, by weight;

the water-miscible organic solvent or, where appropriate, the suspension of the carotenoid or retinoid contains an antioxidant, preferably tocopherol.

13. A suspension as claimed in claim 11, wherein the water-containing medium is a mixture of water and a water-miscible solvent.

14. A method of coloring human and animal foods or beverages, comprising the step of admixing the carotenoid or retinoid suspension as set forth in claim 1.

15. A method of coloring human and animal foods or beverages, comprising the step of admixing the finely dispersed carotenoid or retinoid powder as set forth in claim 7.

* * * * *

UNITED STATES PATENT AND TRADEMARK OFFICE
CERTIFICATE OF CORRECTION

PATENT NO. : 5,895,659
DATED : Apr. 20, 1999
INVENTOR(S) : Lueddecke, et al

It is certified that error appears in the above-identified patent and that said Letters Patent is hereby corrected as shown below:

On the cover page, item [30], "Mar. 11, 1993" should be --Mar. 11, 1996--.

Signed and Sealed this

Twenty-seventh Day of July, 1999

Attest:

Q. TODD DICKINSON

*Attesting Officer*     *Acting Commissioner of Patents and Trademarks*